United States Patent [19]

Yoshida et al.

[11] Patent Number: 4,962,032
[45] Date of Patent: Oct. 9, 1990

[54] ANTI-LAFORA BODY MONOCLONAL ANTIBODY

[75] Inventors: Hajime Yoshida, Sagamihara, Japan; Nobuo Hanai, Mercer Island, Wash.; Akiko Furuya, Machida, Japan

[73] Assignee: Kyowa Hakko Kogyo Co., Ltd., Tokyo, Japan

[21] Appl. No.: 72,293

[22] Filed: Jul. 13, 1987

[30] Foreign Application Priority Data

Jul. 11, 1986 [JP] Japan .................................. 61-163414

[51] Int. Cl.$^5$ .......................... C07K 15/28; C12N 5/20; G01N 33/535; G01N 33/53
[52] U.S. Cl. ............................... 435/240.27; 530/387; 435/7; 435/70.21; 436/548; 935/104; 935/108; 935/110
[58] Field of Search ................. 530/387; 435/240–247, 435/172.2, 68, 7, 70.21; 935/104, 108, 110; 436/548

[56] References Cited

PUBLICATIONS

Yokota, T. et al., "Immunological Homogeneity of Lafora Body, Corpora Amylacea, Basophilic Degeneration in Heart, and Intracytoplasmic Inclusions of Liver and Heart in Type IV Glycogenosis", *Acta Pathol. Jpn.*, 37(6): 941–946, 1987.

Goding, J. W., *Monoclonal Antibodies: Principles and Practice*, Academic Press, Inc., Orlando, 1984, pp. 56–97, 1984.

Sakai, M. et al., "Studies in Myoclonus Epilepsy (Lafora Body Form) II., Polyglucosans in the Systemic Deposits of Myoclonus Epilepsy and Corpora Amylacea", *Neurology*, 20: 160–176, Feb. 1970.

Kamei, J. Clin. Elec. Mic., vol. 17 (1984) 909:10

Robitaille, Brain, vol. 103 (1980) 315:36.

Chemical Abstracts, vol. 84, No. 13, (1976), p. 343, 87689n.

*Primary Examiner*—Margaret Moskowitz
*Assistant Examiner*—Paula Hutzell
*Attorney, Agent, or Firm*—Fitzpatrick, Cella, Harper & Scinto

[57] ABSTRACT

A monoclonal antibody is disclosed capable of reacting with abnormal glycogen from patients with Lafora disease (Lafora bodies) and with abnormal glycogen from patients with type IV glycogenosis but not with normal glycogen, and therefore useful in the diagnosis of Lafora disease and type IV glycogenosis (Andersen's disease).

8 Claims, No Drawings

ANTI-LAFORA BODY MONOCLONAL ANTIBODY

This invention relates to anti-human Lafora body monoclonal antibodies.

Lafora disease (myoclonic epilepsy) and type IV glycogenosis are diseases that are characterised by the accumulation of abnormal glycogens (polyglucosan) in myocardia, nerve cells, liver cells, skin etc., these abnormal glycogens having a long outer side-chain caused by deficiency of alpha-1,4-glucan-6-glycosyltransferase, i.e. the enzyme which forms the branched chain in a molecule of glycogen.

Lafora disease appears to be hereditary and is a syndrome where the clinical symptoms, such as convulsive attack, myoclonic dementia, cerebellar syndrome, character disorder, etc. may be observed before or after puberty, gradually becoming worse, often ending in death after ten or more years on account of general debilitation.

Type IV glycogenosis (Andersen's disease) is a syndrome where a disturbance of growth appears just after birth, associated with hepatomegaly, splenomegaly and hypomyotonia. Ascites is an additional complication, the disease usually ending in death within two years.

It is known that Lafora disease and type IV glycogenosis can be diagnosed pathologically by muscle or liver biopsy, but these methods involve complicated procedures such as treatment by alpha-amylase, treatment by beta-amylase, staining by PAS, etc. and in any case may not result in a definite diagnosis.

In accordance with the present invention, monoclonal antibodies have been developed which are capable of reacting with abnormal glycogen from patients with Lafora disease (Lafora bodies) and with abnormal glycogen from patients with type IV glycogenosis but not with normal glycogen and which are therefore very useful in diagnosis of Lafora disease or type IV glycogenosis.

Such monoclonal antibodies may be obtained according to the present invention by immunising a mammalian animal with a tissue homogenate from patients with Lafora disease and containing Lafora bodies, preferably myocardia homogenates, or Lafora bodies extracted therefrom, fusing spleen cells of the immunised mammalian animal with mammalian myeloma cells, selecting from among the resulting hybridomas a hybridoma cell line producing the required monoclonal antibody, and cultivating the selected hybridoma in a suitable culture medium, or intraperitoneally administering the selected hybridoma to a mammalian animal thereby to cause hybridoma cell propagation in the ascitic fluid in the mammalian animal, followed by separation of the product antibody from the culture medium or the ascitic fluid as the case may be.

As the mammalian animal to be immunised, or from which myeloma cells are to be derived, there may be used mouse, rat, ox or horse, preferably mice.

A method of producing the monoclonal antibodies according to the invention from mice is described in detail below.

(1) Preparation of Antibody-Producing Spleen Cells

Myocardia homogenates from patients with Lafora disease and abnormal glycogen are prepared by the method described in Reference Example 1. Mice are then immunised with the myocardia homogenates.

The immunisation is performed generally by administering the myocardia homogenates (10–100 μg per animal), together with an appropriate adjuvant (e.g. Freund's complete adjuvant, or aluminium hydroxide gel plus B.pertussis vaccine) to 8 or 10 week old BALB/c mice subcutaneously, intravenously or intraperitoneally. Thereafter, the same antigen administration is repeated 2 to 5 times at 1 to 2 week intervals. Four to seven days after each immunisation, the blood is sampled from the eyeground venous plexus and the antibody titer in the serum relative to abnormal glycogen is examined.

Antibody titer determination is performed by a solid phase enzyme linked immunosorbent assay (Enzymelinked Immunosorbent Assay, published by Igaku Shoin, Tokyo 1978) as follows:

Phosphate-buffered saline (PBS; 1.83 g of disodium phosphate, 0.21 g of monopotassium phosphate and 7.65 g of sodium chloride in each liter of distilled water, pH 7.2) containing 10 to 50 μg abnormal glycogen or normal glycogen per ml is distributed into the wells of a 96-well EIA plate (Flow Laboratories) in an amount of 50 μl per well. After allowing it to stand overnight at 4° C., the plate is coated with the antigen. Then, 1% BSA (Bovine serum albumin)-PBS is distributed into the wells (200 μl per plate) and the residual binding site remaining on the bottom of the plate is blocked by BSA. After washing the plate well with PBS, serial dilutions of samples (mouse sera, hybridoma culture supernatants, or purified monoclonal antibodies; each as the first antibody) are distributed into the wells (50 μl per well), followed by overnight standing at 4° C. or at room temperature for 3 to 4 hours.

After washing the wells six times with PBS, a 400-fold dilution of rabbit anti-mouse immunoglobulin IgG-peroxidase conjugate (DAKO PATTS a/s) as the second antibody is distributed into the wells (100 μl per well). The plate is then allowed to stand at room temperature for 2 hours.

After washing well with PBS, an ABTS substrate solution (prepared by dissolving 550 mg of 2,2'-azinobis (3-ethylbenzothiazoline-6-sulfonic acid) diammonium salt in 1 liter of 0.1M citrate buffer (pH 4.2) and adding, just prior to use, hydrogen peroxide to a concentration of 1 μl/ml) is applied, and the colour developed is measured in terms of the absorbance $OD_{415}$ nm. Those mice in which OD value at 415 nm (antibody titer relative to the abnormal glycogen) is not less than $10^3$-fold, compared with OD value at 415 nm of normal mouse serum, are used as supply source of antibody-producing cells.

In preparation for cell fusion, myocardia homogenates from patients with Lafora disease, or abnormal glycogen extracted therefrom, is intraperitoneally administered to the immunised mice in a dose of 10 to 200 μg per animal 3 to 4 days prior to the fusion treatment. The spleens are then extirpated and the spleen cells are prepared for fusion.

(2) Preparation of Myeloma Cells

A mouse-derived established myeloma cell line is used. Suitable examples are the 8-azaguanine resistant mouse (BALB/c-derived) myeloma cell lines P3-X63Ag8-U1 (P3-U1) [Current Topics in Microbiology and Immunology 81, 1–7 (1978)], P3-NSI/1-Ag41 (NS-1) [European J. Immunology 6, 511–519 (1976)], SP2/0-Ag14 (SP-2) [Nature, 276, 269–270 (1978)], P3-

X63-Ag8 653(653) [J. Immunology, 123, 1548–1550 (1979)] and P3-X63-Ag8 (X63) [Nature, 256, 495–497 (1975)], all of which are commercially available. The passage of these cell lines is performed in 8-azaguanine medium [normal medium prepared by adding, to RPMI-1640 medium, glutamine (1.5 mM), 2-mercaptoethanol ($5 \times 10^{-5}$M), gentamicin (10 µg/ml) and fetal calf serum (FCS) (10%), with further supplementation with 8-azaguanine (15 µg/ml)]. The cell line selected for cell fusion should be transferred to normal medium 3 to 4 days before fusion to ensure the cell count of not less than $2 \times 10^7$ on the day of fusion.

(3) Cell Fusion

The spleen cells prepared as in (1) and the myeloma cells obtained in (2) are wahsed well with MEM (product of Nissui Pharmaceutical) or PBS and mixed in a cell number ratio of antibody-producing cells:myeloma cells in the range 5:1 to 10:1 and then subjected to centrifugation. The supernatant is discarded and the cell sediment is loosened up. With stirring a mixture of 1–4 g of polyethylene glycol PEG(1000–4000), 1–4 ml of MEM and 0.5–10 ml of dimethylsulfoxide is added in an amount of 0.1–1.0 ml per $10^8$ spleen cells, and after 0.5–10 minutes, 0.5–3 ml of MEM is added. 0.5–3 ml of MEM is then added several times at 0.5 to 2 minute intervals and then 30–60 ml of MEM is added.

After centrifugation, the supernatant is again discarded and the cell sediment is loosened gently. To the cells is then added 50–200 ml of normal medium and the cells gently suspended with a measuring pipette.

The suspension obtained is distributed in half well volume portions into the wells of an incubation plate. Incubation is carried out in a 3–7% $CO_2$ incubator at 35°–40° C. for 10–30 hours. HAT medium (normal medium supplemented with hypoxanthine ($10^{-5}$–$10^{-3}$M) thymidine ($10^{-6}$–$10^{-4}$M) and aminopterine ($10^{-8}$–$10^{-7}$M) is added to the incubation plate (half of well volume per well) and incubation is conducted for a further 10–30 hours. Thereafter, half of the culture supernatant is discarded and the same volume of fresh HAT medium is added at 10 to 30 hour intervals for 1–3 days. The incubation in the $CO_2$ incubator at 35°–40° C. is continued for 10–14 days.

In those wells in which grown fused colony-forming cells are found, half of the supernatant is discarded and the same volume of HT medium (HAT medium minus aminopterine) is added, followed by medium replacement with fresh portions of HT medium at 10 to 30 hour intervals for 1 to 3 days.

After 3 to 4 days of cultivation in HT medium, a portion of the culture supernatant is collected and assayed for antibody titer relative to abnormal glycogen by the above-mentioned enzyme immunoassay technique. In the wells for which high antibody titer value is obtained, cloning is repeated two to four times by limiting dilution technique. In this way, those clones for which high antibody titer value are stably obtainable are selected as anti-abnormal glycogen monoclonal antibody-producing hybridoma cell lines.

(4) Preparation of Monoclonal Antibodies

Eight- to ten-week old female BALB/c mice treated with pristane (2,6,10,14-tetramethylpentadecane) are intraperitoneally injected with the anti-abnormal glycogen monoclonal antibody-producing hybridoma cells obtained in procedure (3) above at a dose of $2-4 \times 10^{5-7}$ cells per animal. In 10 to 21 days, the hybridoma cells produce ascites carcinoma in the mice. The ascitic fluid is collected, centrifuged to remove solids, subjected to salting out with 50% ammonium sulfate and 40% ammonium sulfate and dialyzed against PBS (pH 7.2) for 1 to 2 days. The dialyzed fraction is used for purification or quantitative determination as a roughly purified monoclonal antibody.

If further purification is needed, the fraction is passed through a DEAE-Sepharose column, Protein-A column or Sephacryl S-300 column and active fractions (IgG, IgM or IgA fractions) are collected.

The isotype or subclass of the antibody is determined by Ouchterlony's method [Seibutsukagaku Jikkenho (Methods in Experimental Biochemistry), Vol. 15, Introduction to Experimental Immunology, P. 74, Gakkai Shuppan Center, 1981].

The quantity of protein is estimated by the Folin's method, followed by calculation based on the absorbance at 280 nm.

The following is a specific example of the above process:

EXAMPLE 1

(1) Preparation of Immunised Mouse Spleen Cells 8-week old female BALB/c mice (Shizuoka Agricultural Cooperative Association for Laboratory Animals) were intraperitoneally administered and immunised with myocardia homogenates from patients with Lafora disease and abnormal glycogen extracted therefrom (100 µg per animal) as an antigen, together with aluminium hydroxide gel (2 mg per animal) and killed *B.pertussis* vaccine (Chiba Serum Institute; $1 \times 10^9$ cells per animal) as an adjuvant. Second and subsequent immunisations at a dose of 100 µg per animal followed at 1 to 2 week intervals.

On and after the third immunisation, the blood was sampled from the eyeground venous plexus 5 to 7 days after the immunisation and the serum of each sample was tested for anti-abnormal glycogen antibody titer by solid phase enzyme linked immunosorbent assay described above.

Those mice in which OD value at 415 nm corresponding to antibody titer relative to abnormal glycogen in serum is not less than $10^3$-fold, compared with OD value at 415 nm of normal mouse serum were further immunised intraperitoneally with abnormal glycogen at a dose of 100 µg per animal. Three days after the immunisation, spleen cells were prepared from such mice and submitted to cell fusion.

(2) Preparation of Myeloma Cells

The 8-azaguanine-resistant murine myeloma cell line P3-U1 was cultivated in 5% $CO_2$ incubator at 37° C. in normal medium [RPMI-1640 supplemented with glutamine (1.5 mM), 2-mercaptoethanol ($5 \times 10^{-5}$M), gentamicin (10 µg/ml) and fetal calf serum (0.1 ml/ml)] to thereby secure not less than $2 \times 10^7$ cells after 4 days.

(3) Hybridoma Production

The immunised mouse spleen cells ($1 \times 10^8$ cells) were washed well with MEM (product of Nissui Pharmaceutical), mixed with the mouse myeloma cells ($2 \times 10^7$ cells) and then subjected to centrifugation (1,200 rpm, 5 minutes).

A mixture of the spleen cells obtained as the sediment and P3U1 cells was loosened up. With stirring at 37° C., 0.5 ml of a mixture of 2 g of polyethylene glycol-1000

(PEG-1000), 2 ml of MEM and 0.7 ml of DMSO was added and 1 minute after, 1 ml of MEM was added. After 5 time-additions of 1 ml of MEM at 1 minute intervals, the whole volume was made up to be 50 ml by addition of MEM. After centrifugation at 900 rpm, the supernatant was discarded and the cell sediment was loosened gently. To the cells was added 100 ml of HAT medium [the aforesaid normal medium supplemented with hypoxanthine ($10^{-4}$M), thymidine ($1.5 \times 10^{-5}$M), and aminopterine ($4 \times 10^{-7}$M)]. The cells were suspended gently in the medium with a 10 ml measuring pipette.

The suspension was distributed into the wells of a 96-well incubation plate (product of Falcon, Becton Dickinson) (200 μg per well). Incubation was carried out in a 5% $CO_2$ incubator at 37° C. for 10 to 14 days.

In those wells in which grown fused colony-forming cells were found, 100 μl of the supernatant was discarded, and 100 μl of HT medium (HAT medium minus aminopterine) was added and incubated at 37° C., followed by medium replacement with fresh portions of HT medium at 24 hour intervals for 2 days in the same manner.

After 4 days of cultivation, a portion of the culture supernatant was collected and assayed for antibody titer against abnormal glycogen by the above-mentioned solid phase enzyme linked immunosorbent assay.

For the wells showing an antibody titer value cloning was repeated twice by the limiting dilution technique. The clone for which antibody titer value was stably obtainable relative to abnormal glycogen was selected as anti-abnormal glycogen monoclonal antibody-producing hybridoma cell line KM-279.

The above monoclonal antibody-producing hybridoma strain KM-279 has been deposited under the terms of the Budapest Treaty with the European Collection of Animal Cell Cultures, Great Britain, on July 3, 1986 as ECACC Deposit No. 86070304.

(4) Monoclonal Antibody Purification

Eight-week old female nude mice (BALB/c nu$^-$/nu$^-$) treated with pristane [intraperitoneally administered with 0.5 ml of 2,6,10,14-tetramethylpentadecane (pristane) and fed for 1 to 2 weeks] were intraperitoneally injected with the hybridoma cell obtained above at a dose of $4 \times 10^6$ cells per animal. The ascitic fluid was collected from the ascitic fluid-bearing mice (4 to 10 ml per animal), centrifuged to remove solids, subjected to salting out with 50% ammonium sulfate, 40% ammonium sulfate, dialyzed against PBS (pH 7.2) for 2 days, and used as a roughly purified monoclonal antibody.

The roughly purified monoclonal antibody was passed through DEAE-Sepharose column and eluted. An IgG fraction was collected and used as purified antibody.

A pathological diagnosis of Lafora disease and type IV glycogenosis is made according to the ordinary immunohistochemical method. A representative example is shown in Example 2.

(5) Antigenic Specificity of the Monoclonal Antibody

The specificity of the purified monoclonal antibody was investigated using solid phase enzyme linked immunosorbent assay. As antigens, abnormal glycogen prepared from myocardia homogenates of Lafora disease patients (Referece Example 1), normal glycogen (product of Nakarai Kagaku) and bovine serum albumin (product of Sigma) were used.

The results are shown in Table 1.

TABLE 1

| Reactive Specificity of KM-279 as determined by ELISA | |
|---|---|
| Antigen | Reactivity ($OD_{415\ nm}$) |
| Abnormal glycogen | 0.990 |
| Normal glycogen | 0.007 |
| Bovine serum albumin | 0.008 |

EXAMPLE 2

Formalin-fixed and paraffin-embedded tissue sections of myocardia or skins from patients with Lafora disease or type IV glycogenosis sliced to a thickness of 5 μm with microtome were mounted on glass slides coated with egg white albumin, dewaxed in xylene, and gradually hydrated with aqueous alcohol.

After washing with deionised water for 5 minutes, endogenous peroxidase was blocked by immersion in 0.3% (wt/vol) hydrogen peroxide in an absolute methanol at room temperature for 30 minutes. The sections were washed with PBS for 20 minutes and incubated with diluted normal horse serum at room temperature for 20 minutes.

Excess serum was soaked up and the anti-abnormal glycogen monoclonal antibody KM-279 (20 μg/ml) was added as the first antibody. The glass was allowed to stand at room temperature for 30 minutes and then washed with PBS. Then a diluted biotin-labelled antibody (Biotin-labelled rabbitant.-mouse IgG antibody) was added to the sections and the glass was allowed to stand for 30 minutes. After washing, an avidin-biotin-peroxidase (product of Vector) was added to the sections and the glass was allowed to stand for 30 minutes. After washing well, the sections were incubated for 2 minutes in a peroxidase substrate solution (mixture of 0.02% hydrogen peroxidase and 0.1% diaminobenzidine tetrahydrochloride in 0.1M Trishydrochloride buffer, pH 7.2) and the reaction was stopped by putting the glass into ice-cold water. The sections were counterstained with hematoxylin, dehydrated in alcohol/water and xylene, settled with Canada balsam and submitted to microscopic examination. As a result, stained figures (Lafora bodies) were widely observed in sections of myocardia or skin from patients with Lafore disease. Similar staining was also observed in sections of myocardia and skin from patients with type IV glycogenosis, indicating the ability of the present monoclonal antibody to react with abnormal glycogen resulting from type IV glycogenosis, as well as abnormal glycogen resulting from Lafora disease (Lafora bodies).

In contrast, no stained figure was observed in sections of myocardia or skins from healthy subjects when the same treatment was carried out.

Reference Example 1

First, 5 to 10 g of myocardia from patients with Lafora disease were cut into small pieces and 20% trichloroacetic acid was added to a final concentration of 10%, with grinding. The sample was then homogenized with homogenizer. The homogenates were centrifuged (3000 rpm, 10 minutes) to recover a supernatant. Double volume of 99.5% ethanol and one-thirtieth volume of saturated potassium chloride solution were added and a mixture was stirred. The sample was centrifuged (3000 rpm, 10 minutes) and a sedimentary fraction was dissolved in deionised water.

The precipitation procedure by ethanol and saturated potassium chloride was repeated three times to recover a sedimentary fraction as the abnormal glycogen.

We claim:

1. A monoclonal antibody of the IgG class that binds with abnormal glycogen from patients with Lafora disease, or with abnormal glycogen from patients with type IV glycogenosis but not with normal glycogen, and obtainable from hybridoma cell line KM-279, E.C.A.C.C. No. 86070304.

2. A hybridoma cell line producing monoclonal antibody according to claim 1.

3. The hybridoma cell line KM-279, ECACC No. 86070304.

4. A diagnostic method for the detection of Lafora disease and type IV glycogenosis which comprises subjecting a tissue sample from a patient to immunoassay with a monoclonal antibody as defined in claim 1 that specifically binds with abnormal glycogen from patients with Lafora disease, or with abnormal glycogen from patients with type IV glycogenosis but not with normal glycogen; and detecting for a positive reaction.

5. An immunohistochemical staining method for determining the presence of abnormal glycogen from patients with Lafora disease, or abnormal glycogen from patients with type IV glycogenosis, which comprises applying to a tissue sample of a patient suspected of having abnormal glycogen resulting from Lafora disease or type IV glycogenosis a monoclonal antibody as defined in claim 1, staining the thus-treated tissue sample to determine the selective reaction of the antibody with abnormal glycogen and the absence of a reaction with normal glycogen, and observing the stained sample.

6. The monoclonal antibody of claim 1, wherein the abnormal glycogen from patients with Lafora disease comprises Lafora bodies.

7. The diagnostic method of claim 4, wherein the abnormal glycogen from patients with Lafora disease comprises Lafora bodies.

8. The immunohistochemical staining method of claim 8, wherein the abnormal glycogen from patients with Lafora disease comprises Lafora bodies.

* * * * *

UNITED STATES PATENT AND TRADEMARK OFFICE
CERTIFICATE OF CORRECTION

PATENT NO. : 4,962,032

DATED : October 9, 1990

INVENTOR(S) : HAJIME YOSHIDA, ET AL.

It is certified that error appears in the above-identified patent and that said Letters Patent is hereby corrected as shown below:

Column 6, line 30, "(Biotin-labelled rabbitant.-mouse IgG antibody)" should read --(Biotin-labelled rabbit ant.-mouse IgG antibody)--.

Column 8, line 20, "claim 8," should read --claim 5,--.

Signed and Sealed this

Fifth Day of March, 1991

Attest:

HARRY F. MANBECK, JR.

Attesting Officer

Commissioner of Patents and Trademarks